(12) United States Patent
Goldstein et al.

(10) Patent No.: US 8,170,228 B2
(45) Date of Patent: May 1, 2012

(54) METHODS AND DEVICES FOR HEARING DAMAGE NOTIFICATION AND INTERVENTION II

(75) Inventors: Steven W. Goldstein, Delray Beach, FL (US); John P. Keady, Boca Raton, FL (US)

(73) Assignee: Personics Holdings Inc., Boca Raton, FL (US)

( * ) Notice: Subject to any disclaimer, the term of this patent is extended or adjusted under 35 U.S.C. 154(b) by 1182 days.

(21) Appl. No.: 11/943,161

(22) Filed: Nov. 20, 2007

(65) Prior Publication Data

US 2008/0130906 A1 Jun. 5, 2008

Related U.S. Application Data

(60) Provisional application No. 60/824,432, filed on Nov. 20, 2006.

(51) Int. Cl.
*H04R 29/00* (2006.01)
*G10K 11/16* (2006.01)
*H03B 29/00* (2006.01)

(52) U.S. Cl. ........... 381/71.6; 381/56; 381/57; 381/163; 381/317; 381/318

(58) Field of Classification Search .................. 381/56, 381/57, 163, 317, 318, 71.6
See application file for complete search history.

(56) References Cited

U.S. PATENT DOCUMENTS

| | | | |
|---|---|---|---|
| 3,987,245 A | | 10/1976 | Fasen et al. |
| 4,833,719 A * | | 5/1989 | Carme et al. ................... 381/72 |
| 5,812,678 A * | | 9/1998 | Scalise et al. .................. 381/67 |
| 6,379,314 B1 | | 4/2002 | Horn |
| 6,408,078 B1 * | | 6/2002 | Hobelsberger ................. 381/96 |
| 6,456,199 B1 | | 9/2002 | Michael |
| 6,735,316 B1 * | | 5/2004 | Wurtz ............................ 381/74 |
| 6,840,908 B2 | | 1/2005 | Edwards et al. |
| 6,912,286 B1 | | 6/2005 | Daly |
| 6,925,620 B2 | | 8/2005 | Elzinga |
| 7,039,195 B1 * | | 5/2006 | Svean et al. .................. 381/71.6 |
| 7,499,555 B1 * | | 3/2009 | Isvan ........................... 381/71.6 |
| 7,817,803 B2 * | | 10/2010 | Goldstein ....................... 381/56 |
| 2004/0234094 A1 * | | 11/2004 | Saunders et al. .............. 381/380 |
| 2005/0254665 A1 | | 11/2005 | Vaudrey |
| 2005/0254667 A1 | | 11/2005 | Michael |
| 2007/0129828 A1 | | 6/2007 | Lee |
| 2008/0205660 A1 * | | 8/2008 | Goldstein ...................... 381/60 |

OTHER PUBLICATIONS

Begault, Durand R., "Direct Comparison of the Impact of Head Tracking, Reverberation, and Individualized Head-Related Transfer Functions on the Spatial Perception of a Virtual Speech Source", J. Audio Eng. Soc., vol. 49, No. 10 (Oct. 2001), 904-916. Fligor, Brian J., "Output Levels of Commercially Available Portable Compact Disc Players and the Potential Risk to Hearing", Ear & Hearing, vol. 25, No. 6 (2004), 513-527.
Melnick William, "Human Temporary Threshold Shift (TTS) and Damage Risk", J. Acoust. Soc. Am., vol. 90, No. 1 (Jul. 1991), 147-154.
Zotkin, Dmitry N., "Creation of Virtual Auditory Spaces", Proc. IEEE, ICASSP 2002, vol. 2 (May 2002), 2113-2116.

* cited by examiner

*Primary Examiner* — Victor A Mandala
(74) *Attorney, Agent, or Firm* — RatnerPrestia

(57) ABSTRACT

Methods of monitoring sound pressure level are provided. A method of monitoring sound pressure level includes: measuring a first sound pressure level in the ear canal; measuring a second sound pressure level out of the ear canal; calculating a first sound pressure level dose using the first sound pressure level, where if the first sound pressure level is below a permissible sound level a recovery function is used to calculate the first sound pressure level dose; and calculating a second sound pressure level dose using the second sound pressure level.

23 Claims, 5 Drawing Sheets

METHODS AND DEVICES FOR HEARING DAMAGE NOTIFICATION AND INTERVENTION II

CROSS-REFERENCE TO RELATED APPLICATIONS

This application claims the priority benefit of 60/824,432, under 35 U.S.C. §119(e), filed 20 Nov. 2006, which is incorporated herein by reference in its entirety.

FIELD OF THE INVENTION

The invention relates in general to methods and devices for notifying a user or intervening in the audio dosage level a user receives, and more particularly, though not exclusively, a method and device for monitoring the acoustic sound pressure level and calculating a total sound pressure level (SPL) dosage value.

BACKGROUND OF THE INVENTION

With the advent of an industrial society, people are exposed to noise pollution at greater and greater levels; both from background, such as street traffic, airplanes, construction sites and intentional exposure to high sound levels such as cell phones, MP3 players, and rock concerts. Studies show that ear damage, leading to permanent hearing impairment is not only increasing in the general population, but increasing at a significantly faster rate in younger populations.

The potential for hearing damage is a function of both the level and the duration of exposure to the sound stimulus. Safe listening durations at various loudness levels are known, and can be calculated by averaging audio output levels over time to yield a time-weighted average. Standard damage-risk guidelines published by OSHA, NIOSH or other agencies are known. This calculation can be even further improved by accounting for aspects of the playback scenario, specifically the characteristics of the sound source and their proximity to the listener's ear.

Studies have also indicated that hearing damage is a cumulative phenomenon. Although hearing damage due to industrial or background noise exposure is more thoroughly understood, the risk of exposing one's self to excessive noise, especially with the use of headphones has also been recently studied. Protecting the ear from ambient noise is primarily done with the use of static earplugs that attempt to shield the inner ear from excessively high decibel noise. Background noise canceling earphones such as those produced by Bose and others, attempt to protect the ear from excessive ambient noise by producing a counter noise wave to cancel out the ambient noise at the ear. These prior art devices have been less than satisfactory because they do not completely prevent high decibel noise from reaching the ear, and do not account for the duration of exposure to harmful sounds at the ear.

It is also known from the prior art to provide active noise reduction at the ear to protect the ear from exposure to loud noises as disclosed in U.S. patent Application No. US2005/0254665. The art actively attenuating noise reaching the inner ear utilizing a control; a connection with an earpiece and attenuating the noise to the ear. However, there is no monitoring of the noise over time to account for the cumulative effect. Furthermore, there is no accounting for any restorative effects within the ear for sound level exposures which are sufficiently low to allow recovery, rather than destruction.

Dosimeters, such as that described in U.S. published Application No. US2005/0254667 are known. The device periodically measures prior sound level in the ambient environment. However, the device does not take into account the cumulative effect of the noise over multiple incidences of exposure (e.g., one day to the next) or the effect of any restorative period. Furthermore, no remedial action is automatically taken as a result of the readings.

It is also known from the prior art that headphones for consumer electronics have been provided with a predetermined maximum output level in an attempt to prevent ear damage. This approach is ineffective as it does not take into account listening duration and the calculation of risk for auditory injury. Other headphones are maximum-limited to produce levels that can still result in significant overexposure given enough time, or limit the user to levels, which may not be sufficient to achieve an adequate short term listening level. In the latter case, consumer acceptance for the protective gear could be severely limited and a product would fail to survive in a competitive market and therefore be of no use.

Another alternative known in the art is to reduce the headphone output levels by increasing earphone impedance via an accessory placed between the media player and the earphones. The limitation of this approach is that it gives no consideration to the duration of exposure, and again either the user's chosen listening level cannot be achieved because the maximum level is too limited, or the level is sufficient to allow the user access to high enough sound levels, but risk overexposure due to potential duration of use.

It is known from U.S. Publication No. 2007/0129828 to provide automated control of audio volume parameters in order to protect hearing. A method of operating a media player includes the step of playing back audio media and refining a maximum volume parameter for the playing of the media by the media player. The refining is based at least in part on the playback of audio media during a time period existing prior to the execution of refining the maximum volume allowed. The refinement is intended to minimize harm to the user's hearing.

Applicants cannot confirm that such an approach has been commercialized. However, even if commercialized, it suffers from the shortcomings that the refinement is based on a theoretical noise volume delivered to the ear as a function of the output signal of the device and parameters of the earpiece connected to the device and is based upon a credit system based on volume. There is no measurement of the actual noise delivered to the ear. Furthermore, the calculation does not take into account the ambient noise of the device user nor the noise reduction rate of the earpiece relative to the ambient noise. In other words, the actual volume level to which the ear is exposed is not taken into account. Accordingly, a severe miscalculation of the actual ear exposure, and resulting ear harm, may exist as a result of use of this related art method. Additionally the credit system is not described in detail sufficient for one of ordinary skill to construct the device. For example U.S. Publication No. 2007/0129828 refers to Cal-OSHA profiles, and states in the same paragraph that Cal-OSHA appear to be rudimentary and does not deal with exposure "in a sophisticated way with varying exposure over time" and does not " . . . account for recovery." However, U.S. Publication No. 2007/0129828 states in one example " . . . the maximum allowed volume is determined based upon determined credits with reference to a profile such as profiles provided by . . . (Cal-OSHA) . . . " However, U.S. Publication No. 2007/0129828, stated that Cal-OSHA doesn't take into effect recovery, and additionally fails to refer to any detailed recovery calculation. Additionally, the credit system is based upon volume, rather than a predicted sound pressure level (PSPL) emitted by a speaker, and thus is an inaccurate predictor of sound pressure level (SPL) experienced by a user's ears due to emissions from the speaker.

Recent studies indicate that prolonged headphone listening at high volumes can cause Hearing Damage. Several cases have been documented, some even spawning lawsuits. Although Hearing Damage due to industrial noise exposure is more thoroughly understood, the risks associated with listening to headphones have also been studied. Researchers have attempted to determine headphone listening level recommendations based on experiments and accepted standards (Fligor and Cox, 2004).

However, no conventional art system monitors the SPL Dosage that is a combination of the attenuated ambient audio signal (passing through an earpiece) and the audio signal produced by an ear canal receiver, and compares the SPL dosage to an unprotected ear, and notifies a user when the earpiece should be switched to the other ear to minimize hearing damage to an unprotected ear.

SUMMARY OF THE INVENTION

At least one exemplary embodiment is directed to a method of monitoring sound pressure level comprising: measuring a first sound pressure level in the ear canal; measuring a second sound pressure level out of the ear canal; calculating a first sound pressure level dose using the first sound pressure level, where if the first sound pressure level is below a permissible sound level a recovery function is used to calculate the first sound pressure level dose; and calculating a second sound pressure level dose using the second sound pressure level.

At least one exemplary embodiment is directed to a sound pressure level monitoring device comprising: a first input; and a logic circuit, where the logic circuit calculates a sound pressure level equivalent of the first input and calculates a sound pressure level dose, which includes a recovery function if a sound pressure level total is less than a permissible sound level.

At least one exemplary embodiment is directed to a method of sound pressure level measurement comprising: calculating a sound pressure level equivalent for a drive signal; calculating a sound pressure level for a measured signal; calculating a total sound pressure level dose from a total sound pressure level, where if the total sound pressure level is less than a permissible sound level then a recovery function is used in calculation of the total sound pressure level dose; comparing the total sound pressure level dose to a threshold value; and modifying the drive signal if the total sound pressure level dose exceeds the threshold value, where if a new total sound pressure level dose is calculated using the modified drive signal the new total sound pressure level dose is less than the threshold value.

At least one exemplary embodiment is directed to an earpiece comprising: a microphone in an earpiece; and data readable storage medium, where upon activating a recording mode audio signals measured from the microphone are stored on data readable medium.

Further areas of applicability of exemplary embodiments of the present invention can become apparent from the detailed description provided hereinafter. It should be understood that the detailed description and specific examples, while indicating exemplary embodiments of the invention, are intended for purposes of illustration only and are not intended to limit the scope of the invention.

BRIEF DESCRIPTION OF THE DRAWINGS

Embodiments of the present invention can become apparent from the following detailed description, taken in conjunction with the drawings in which.

DETAILED DESCRIPTION OF EXEMPLARY EMBODIMENTS OF THE PRESENT INVENTION

Figure 1:
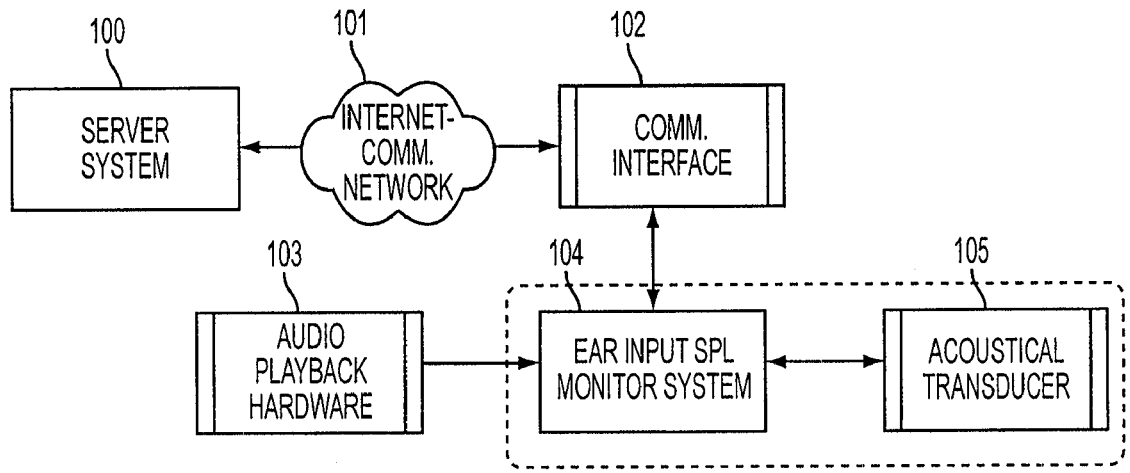
FIG. 1 illustrates the system according to the present invention.

The following description of exemplary embodiment(s) is merely illustrative in nature and is in no way intended to limit the invention, its application, or uses.

Processes, methods, materials and devices known by one of ordinary skill in the relevant arts may not be discussed in detail but are intended to be part of the enabling discussion where appropriate for example the generation and use of transfer functions.

In all of the examples illustrated and discussed herein any specific value or functions, for example generating a SPL Dose, should be interpreted to be illustrative only and non limiting. Thus, other examples of the exemplary embodiments could have different values, use different functions, and/or other averaging or frequency dependent weighting functions.

Notice that similar reference numerals and letters refer to similar items in the following figures, and thus once an item is defined in one figure, it may not be discussed for following figures.

Exemplary Embodiment Summary

At least one exemplary embodiment of the present invention can be applied to almost any Audio Playback scenario, informing the listener about the potential for Hearing Damage inherent to that scenario. Because at least one exemplary embodiment accounts for Environmental Noise, it can be applied to hearing protection devices as well.

The potential for Hearing Damage associated with a sound stimulus is a function of the sound level, the spectral content, and the duration of that stimulus. Therefore, noise exposure is commonly expressed as the 8-hr time-weighted average (TWA) of the A-weighted (e.g., frequency dependent functions, see ISO standard) sound pressure levels. In industrial workplace settings, it is common to measure exposure to Environmental Noise in terms of a noise dose-the TWA noise exposure for an individual expressed as a percentage of the total allowable daily noise exposure (i.e. 100% noise dose is equal to 85 dBA 8-hr TWA). Exemplary embodiments within present a variation on the noise dose measure titled the SPL Dose.

This measure accounts for Audio Playback as well as Environmental Noise in modeling the potential for Hearing Damage for a particular user. Unlike the noise dose, which resets at the end of each workday, the SPL Dose can be cumulativepersisting from day to day. During moderate to intense Audio Playback and/or Environmental Noise, the SPL Dose will increase. During time periods of negligible environmental noise and no audio playback, the SPL Dose will decrease according to an Ear Recovery Function. This measure provides an enhanced model of an individual's potential risk for Hearing Damage.

At least one exemplary embodiment within discloses a system for calculating a Safe Listening Duration for a given Audio Playback scenario. The Safe Listening Duration calculation is based on audiological research and recommendations, the user's SPL Dose, and current Audio Playback and Environmental Noise levels.

In further exemplary embodiments, input acoustical transducers convey environmental auditory stimuli to the user through the audio signal path. This eliminates the need for the user to remove their Headphones during a conversation. Furthermore, this allows the system to double as a linear-frequency-response hearing protection apparatus-appropriate for loud rock concerts or occupational noise exposure.

Furthermore, at least one exemplary embodiment within discloses methods for retrieving SPL Exposure Histories recorded in the data memory of the Personal Hearing Damage Intervention System. These histories describe the user's listening habits-how often, how long, and how intense the user listens to music or other audio content as well as information about that audio content including spectral analysis and metadata. The histories also describe the user's exposure to environmental noise over time. Coupled with the user's registration information, the SPL Exposure Histories could prove to be a valuable research tool in the field of audiology, noise pollution study, and other fields.

Additional exemplary embodiments disclose a method for sharing a digital audio transmission amongst enabled devices over a wireless communications system. The same wireless communications apparatus enables the system to communicate with capable devices, retrieving audio signals or other data from outside sources. Further exemplary embodiments describe enabled devices sharing recorded Listening Habit Histories and Control Data.

At least one further exemplary embodiment includes a language translation system for translating a speech signal present in the Environmental Audio to another language and presenting a synthesized speech translation to the user.

Additionally at least one exemplary embodiment can include a detailed registration process, through which the Personal Hearing Damage Intervention system can be customized for an individual user. In several exemplary embodiments, head-related transfer function (HRTF) data is included as part of this customization. Furthermore, the registration process includes a comprehensive legally-compliant, state-specific Informed Consent system for collecting and storing the Informed Consent of users.

Additional exemplary embodiments facilitate the sharing of audiological data, listening trends data, and other data relevant to research and marketing.

Thus, exemplary embodiments have applications in consumer electronics, professional audio equipment, industrial safety equipment, hearing aid equipment, mobile phone systems, avionics, and other areas.

Examples of Terminology

Note that the following non-limiting examples of terminology are solely intended to aid in understanding various exemplary embodiments and are not intended to be restrictive of the meaning of terms nor all inclusive.

Acoustic Isolation Cushion: An "Acoustic Isolation Cushion" can be defined as a circum-aural or intra-aural device that provides acoustic isolation from Environmental Noise. Acoustic Isolation Cushions can be included as part of a Headphones system, allowing the output of the acoustical transducers to reach the ear unimpeded, but still providing acoustic isolation from Environmental Noise.

Acoustic Transducer: An "Acoustic Transducer" can be defined as a device that converts sound pressure level variations into electronic voltages or vice versa. Acoustic Transducers include microphones, loudspeakers, Headphones, and other devices.

Audio Playback: "Audio Playback" can be defined as the auditory stimuli generated when Playback Hardware reproduces audio content (music, spoken word, etc) for a listener or a group of listeners. A listener using Headphones and a personal music player to acoustically perceive a digital audio file is a common Audio Playback scenario.

Audition: "Audition" can be defined as the process of detecting sound stimulus using the human auditory system (the ear). This includes the physical, psychophysical, psychoacoustic, and cognitive processes associated with the perception of acoustic stimuli.

Attenuation: "Attenuation" can be defined as a reduction of the signal output level either by linear gain reduction, by dynamic range reduction, or a combination of both or termination of all playback sound.

Client: A "Client" can be defined as a system that communicates with a Server, usually over a communications network, and directly interfaces with a user.

Control Data: "Control Data" can be defined as information that dictates the operating parameters for a system or a set of systems. For the Personal Hearing Damage Intervention system described in the embodiments within, Control Data includes minimum audio input threshold parameters, default or specific acoustical transducer characteristics, the voltage output to a Real-Ear Level transfer function, the time-weighted average SPL exposure calculation parameters, SPL Dose calculation parameters, the Safe Listening Duration calculation parameters, the instantaneous Environmental Noise level threshold, the instantaneous Audio Playback level threshold, and any filtering parameters that relate to Audiogram compensation, inverse Headphone response, personal preferences, audiological recommendations or other data.

Ear Mould Style: "Ear Mould Style" can be defined as a description of the form factor for an intra-aural device (i.e. hearing aids). Ear Mould Styles include completely in the canal (CIC), in the canal (ITC), in the ear (ITE), and behind the ear (BTE).

Ear Recovery Function: An "Ear Recovery Function" can be defined as a function describing the rate at which the human auditory system recovers from excessive SPL exposure. In the Hearing Damage Intervention System the Ear Recovery Function is used in the SPL Dose calculation, dictating how quickly the SPL Dose decreases in the absence of Audio Playback or significant Environmental Noise.

Effective Quiet: "Effective Quiet" can be defined as sound levels considered to not contribute to noise-induced permanent threshold shift (NIPTS); 76-78 dBA (Melnik, 1991) for broadband noise.

Environmental Audio: "Environmental Audio" can be defined as auditory stimuli of interest to the user in the environment where the user is present. Environmental Audio includes speech and music in the environment.

Environmental Noise: "Environmental Noise" can be defined as the auditory stimuli inherent to a particular environment where the user is present. The drone of highway traffic is a common example of Environmental Noise. Note that Environmental Noise and Audio Playback are two distinct types of auditory stimuli. Environmental Noise does not typically include Music or other audio content.

Environmental Noise Exposure History: "Environmental Noise Exposure History" can be defined as a record of a user's exposure to Environmental Noise over time. This record is very detailed, including Real-Ear Level SPL data, timer system data, Acoustics Isolation Cushion characteristics, the state of Audio Playback, and other data. The Environmental Noise Exposure History is a component of SPL Exposure History.

Exchange Rate: An increment of sound level, expressed in decibels (dB), that requires halving the exposure time, or a decrement of decibels that allows the doubling of exposure time. For example, a 3-dB exchange rate indicates that for every 3-dB increase in sound level, half the exposure time is allowed.

Generic HRTF: A "Generic HRTF" can be defined as a set of HRTF data that is intended for use by any Member. A Generic HRTF can provide a generalized model of the parts of the human anatomy relevant to audition and localization, or simply a model of the anatomy of an individual other than the Member. The application of Generic HRTF data to Audio Content provides the least convincing Spatial Image for the Member, relative to Semi-Personalized and Personalized HRTF data. Generic HRTF data is generally retrieved from publicly available databases such as the CIPIC HRTF database.

Headphones: "Headphones" are a set of Acoustical Transducers intended as personal listening devices that are placed either circum-aural or intra-aural according to one of the Ear Mould Styles. This includes the Playback Hardware commonly referred to as "earbuds," or "headphones," as well as other devices that meet the above definition such as advanced eye-wear that includes. Acoustical Transducers (i.e. Dataview). Headphones may also include stereo input Acoustic Transducers (microphones) included as part of the Ear Mould Style form factor.

Hearing Damage: "Hearing Damage" can be defined as any injury to the hearing mechanism, including conductive and sensorineural decrement in hearing threshold levels, either temporary (as in Temporary Threshold Shift [TTS]) or permanent (as in Permanent Threshold Shift [PTS]). Hearing damage can also include the occurrence of tinnitus, hypersensitivity to moderate to intense sound (hyperacusis or recruitment), and abnormal pitch perception (diplacusis) as a result of noise exposure above Effective Quiet.

HRTF: "HRTF" is an acronym for head-related transfer function-a set of data that describes the acoustical reflection characteristics of an individual's anatomy relevant to audition. Although in practice they are distinct (but directly related), this definition of HRTF encompasses the head-related impulse response (HRIR) or any other set of data that describes some aspects of an individual's anatomy relevant to audition.

Informed Consent: "Informed Consent" can be defined as a legal condition whereby a person can be said to have given formal consent based upon an appreciation and understanding of the facts and implications associated with a specific action. For minors or individuals without complete possession of their faculties, Informed Consent includes the formal consent of a parent or guardian.

Listening Habits History: "Listening Habits History" can be defined as a record of a user's listening habits over time. This record is very detailed, including Real-Ear Level SPL data, timer system data, and time between listening sessions. The Listening Habits History may also include information about the audio content used in Audio Playback such as metadata and spectral content. The Listening Habits History is a component of SPL Exposure History.

Music: "Music" can be defined as a form of expression in the medium of time using the structures of tones and silence to create complex forms in time through construction of patterns and combinations of natural stimuli, principally sound.

Noise Dose: The amount of exposure to intense Environmental Noise relative to the amount considered allowable exposure, for which 100% and above represents exposures that are hazardous. Where Noise Dose is expressed as $D=[C_1/T_1+C_2/T_2+\ldots+C_n/T_n]\times 100$; D=Noise Dose, $C_n$=total exposure time at a specified sound level, and $T_n$=exposure duration for which sound at this level becomes hazardous.

Playback Hardware: Any device used to play previously recorded or live streaming audio. Playback Hardware includes Headphones, loudspeakers, personal music players, mobile phones, and other devices.

Personalized HRTF: A "Personalized HRTF" can be defined as a set of HRTF data that is measured for a specific Member and unique to that Member. The application of Personalized HRTF data to Audio Content creates, by far, the most convincing Spatial Image for the Member (Begault et. al. 2001, D. Zotkin, R. Duraiswami, and L. Davis 2002).

Real-Ear Level (REL): "Real-Ear Level" can be defined as a measure of the sound pressure level at the input to an individual's hearing system. Real-Ear Level is sometimes referred to as eardrum SPL or tympanic membrane SPL (TM SPL) in audiology. Real-Ear Level is abbreviated as REL and usually measured in units of dB SPL or dBA.

Relative Audiogram: A "Relative Audiogram" can be defined as a measured set of data describing a specific individual's hearing threshold level as a function of frequency. A Relative Audiogram is only an approximate Audiogram, leaving more complete Audiogram analysis to qualified audiologists.

Safe Listening Duration: "Safe Listening Duration" can be defined as a measurement of time indicating how long an individual can listen to Audio Playback before some threshold for Hearing Damage potential is exceeded. The threshold for Hearing Damage potential is expressed in terms of SPL Dose and is included as part of the Control Data. This threshold is based on audiological research and standards. A default threshold, which may correspond to a specific age range, can be customized through a registration process.

Semi-Personalized HRTF: A "Semi-Personalized HRTF" can be defined as a set of HRTF data that is selected from a database of known HRTF data as the "best-fit" for a specific user. Semi-Personalized HRTF data is not necessarily unique to one user, however interpolation and matching algorithms can be employed to modify HRTF data from the database to improve the accuracy of a Semi-Personalized HRTF. The application of Semi-Personalized HRTF data to Audio Content provides a Spatial Image that is improved compared to that of Generic HRTF data, but less effective than that of Personalized HRTF data. The embodiments within speak to a variety of methods for determining the best-fit HRTF data for a particular Member including anthropometrical measurements extracted from photographs and deduction.

Server: A "Server" can be defined as a system that controls centrally held data and communicates with Clients.

SPL Dose: "SPL Dose" can be defined as a measurement indicating an individual's cumulative exposure to sound pressure levels over time. This term is derived from the term Noise Dose, but unlike Noise Dose, SPL Dose accounts for exposure to Audio Playback as well as exposure to Environmental Noise. An SPL Dose is expressed as a percentage of some maximum time-weighted average for sound pressure level exposure (i.e. a SPL Dose of 100% indicates the user has reached the time-weighted average SPL exposure limit). Although the time period for Noise Dose measurements usually corresponds to the length of a workday (usually 8 hours), SPL Dose is cumulative and therefore has no time period. The SPL Dose increases during Audio Playback and for moderate to high Environmental Noise levels, above Effective Quiet. The SPL Dose decreases over time when Environmental Noise levels are negligible and no Audio Playback is present (see FIG. 5), below Effective Quiet. The thresholds and rates of change associated with the SPL Dose are derived from acoustic overexposure criteria and recovery time data (Ear Recovery Function) found in audiological research.

For example SPL Dose can be expressed as:

SPL Dose(n)=SPL Dose(n−1)+(Update_Epoch(n)/Time_100%) where SPL Dose(n−1) is the SPL Dose calculated during the last epoch; Update_Epoch is the time (in hours) since the last SPL Dose was calculated. As described above, Update_Epoch can be adaptive, e.g., shortened when the sound pressure level is louder; and Time_100% (n), the time period remaining for safe exposure is determined by the equation:

Time_100% can be expressed as:

$$\text{Time\_100\%}(n) = 24 \text{ hours}/(2^{(L-PSL)/3})$$

where L=sound level (in dB) of the combination of Environmental Noise and Audio Playback. Note that PSL is the permissible sound level (e.g., PSL=80 dB).

If the differential A=SPL_W(n)−PSL is less than zero, within measurement error, then this is considered a restorative quiet, then the n-th SPL dose is determined as:

$$\text{SPL Dose}(n) = \text{SPL Dose}(n-1) * e^{(-\text{Update\_epoch}/\tau)}$$

Where: τ (referred to as "tau" in the following diagrams) can vary (e.g., equal to about 7 hours). In some exemplary embodiments, tau is adaptive for different users. In at least one exemplary embodiment, the level change threshold (e.g., measurement error) is set at substantially 0.9-1.0 dB.

It should be noted, as can be seen from the equation, that the time value becomes more important than the sound pressure level as updates are spread apart. However, this is to protect overexposure to harmful sounds because a less accurate sample size must account for the unknown. The wider the periodicity, the less accurate determination of actual exposure. Infrequent updates of the SPL Dose assume a relatively constant sound level, ignoring transients (e.g. spikes) and intervening restorative periods. Accordingly, sound pressure level and epoch periodicity are weighed against each other to protect the ear.

SPL Exposure History: "SPL Exposure History" can be defined as a record of a user's exposure to sound pressure levels over time. This record is very detailed, including Real-Ear Level data, listening duration data, time between listening sessions, absolute time, SPL Dose data, and other data. SPL Exposure History includes both Listening Habits History and Environmental Noise Exposure History.

Time-weighted Average (TWA): "Time-weighted Average" can be defined as the average of different exposure levels during a time period. For noise, if using an 85 dBA exposure limit for 8-hours and a 3-dB Exchange Rate, the TWA can be expressed as a function of Noise Dose according to TWA=10×Log$_{10}$(D/100)+85, where D=Noise Dose.

Exemplary Embodiments

A typical usage scenario for the preemptive SPL monitoring system is illustrated in FIG. 1. The Personal Hearing Damage Intervention system [104] is inserted into the audio signal path immediately after the audio playback device [103] and immediately before the acoustical transducers [105]. This allows the system to monitor the Real-Ear Level (through direct measurement or calculation) and apply any alterations or attenuations to the audio signal path.

The SPL monitoring system is capable utilizing a communications interface [102] and a communications network [101] to exchange information with a server system [100]. Information exchanged could include control data, listening habits data, system updates, usage statistics, and other data.

Figure 2:
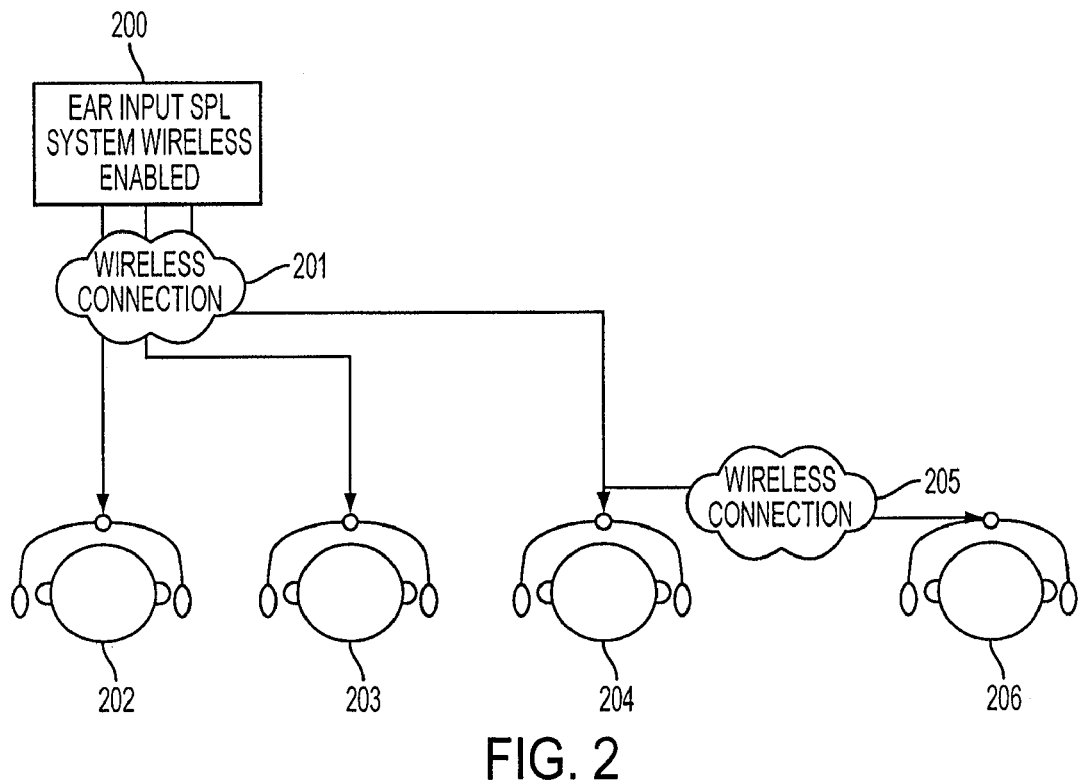
FIG. 2 shows how the present invention might be applied to share audio signals among multiple users.

A specialized usage scenario for the Personal Hearing Damage Intervention system is illustrated in FIG. 2. In this scenario, the communications interface for the system utilizes some wireless communications protocol capable of transmitting audio data. One system acts as a source [200], transmitting audio data wirelessly [201] to other enabled devices [202-203]. An enabled system can act as both a receiver and a source [204] by re-broadcasting audio data [205] to additional systems [206], extending the range of a transmission. Enabled systems can scan for, receive, and create audio transmissions.

Figure 3:
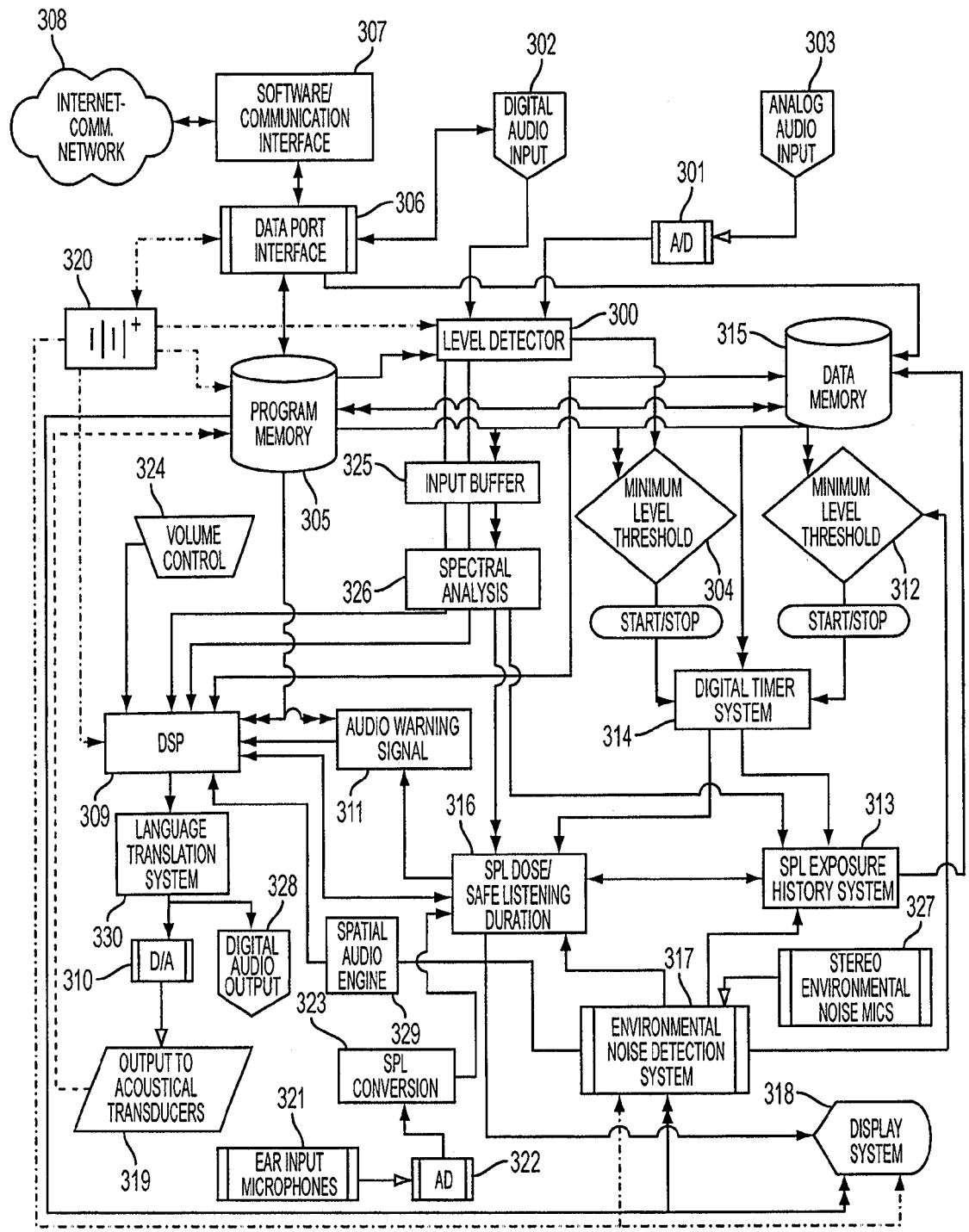
FIG. 3 illustrates in more detail the portion of the system of the present invention that operates on the client side, as a piece of hardware, software, or firmware.

A more detailed illustration of the Personal Hearing Damage Intervention System is provided in FIG. 3. The system is capable of accepting an analog audio input [303], a digital audio input [302], or an audio transmission from the data port interface [306]. Analog audio inputs are converted to digital audio via analog-to-digital (A/D) converter [301].

An input level detector [300] monitors the audio input level to the system. Once a minimum audio input threshold [304] is crossed in the positive direction a digital timer system [314] is prompted. When the minimum threshold is crossed in the negative direction (signal falls below the minimum threshold) the digital timer system [314] is prompted again. These prompts to the timer system [314] indicate start and stop times for listening durations and can be recorded as part of a particular user's listening habits history in the data memory [315].

An input buffer [325] introduces a short time delay in the audio signal path allowing excessively loud signals to be automatically attenuated before they are reproduced as sound pressure levels by the acoustical transducers.

A spectral analysis process [326] examines the spectral content of the audio signal path, taking a closer look for signals that may require attenuation. The spectral contents of the audio signal path are stored periodically as part of the Listening Habits History component of the SPL Exposure History.

In one embodiment of the present invention, the start time and current time indicated by the digital timer system [314] and the audio input level detector [300] are used in the calculation of a Safe Listening Duration [316]. Based on the input level detector [300] and a default set of acoustical transducer characteristics, the Real-Ear Level is estimated. This estimate can be improved with a specific set of acoustical transducer characteristics.

Alternatively, a pair of Real-Ear Level microphones [321] can be converted to digital audio (via analog-to-digital converter [322]) and used to directly measure the SPL input [323] at a user's ear. This data, along with the timer system [314] can be used in the calculation of a Safe Listening Duration [316].

An Environmental Noise detection system [317] receives input from an Environmental Noise microphone [327]. The detection system includes Environmental Noise exposure in the calculation of SPL Dose and the Safe Listening Duration calculation [316].

The Environmental Noise detection system [317] connects to a spatial audio engine [329] that ensures the preservation of spatial audio cues present in any Environmental Audio signals. The spatial audio engine [329] then connects to the digital signal processor (DSP) [309] where Attenuated Audio Playback signals and Environmental Audio signals are mixed.

The Safe Listening Durations, ambient noise levels, SPL Dose and Real-Ear Level used in [316] are sent to the SPL Exposure History system [313]. The SPL Exposure History is then stored in the data memory [315]. When available, metadata describing the audio content associated with the stored Listening Habits History is retrieved through the data port [306] and stored in data memory.

The calculated Safe Listening Duration can be indicated by a display system [318] or conveyed to the user through an audio warning signal [311]. A combination of both methods can also be employed. The audio signal path can also be automatically attenuated using the digital signal processor [309]. This attenuation could be in the form of dynamic range compression, gain reduction, or total gain reduction (no audio).

A volume control interface [324] allows the user to manually control the volume of the audio signal path using the digital signal processor [309]. Such changes in volume propagate to the SPL Dose and Safe Listening Duration calculations [316].

A digital signal processor [309] allows for the application of an arbitrary filter to the audio signal path, which might be related to user preferences, user Relative Audiogram, Playback Hardware response, or any other appropriate data.

An audio signal path connects the digital signal processor [309] and the data memory [315] to allow for the recording and playback of audio content.

The digital signal processor [309] enables the mixing of an audio warning signal [311] with the audio signal path.

A program memory storage device [305] contains Control Data for the entire system in FIG. 3. The program memory is initialized with some default Control Data. The Control Data can be updated through the data port interface [306] possibly using software on the user's personal computer to communicate with a Server across some communications network [308] (i.e. the Internet).

Alternatively, the Control Data updates can be retrieved from a Server using a communications interface [307], a communications network [308], and the data port [306]. The communications interface would most likely consist of a piece of software running on a client personal computer, and the communications network would most likely be the Internet. These Control Data updates can be automatic, part of a user registration process, or both.

The data port interface [306] may use any appropriate communications protocol, wired or wireless. Examples include universal serial bus (USB), firewire, 802.11, and Bluetooth communication protocols. A digital to analog converter [310] converts the audio signal path to analog voltages to be output to some acoustical transducers [319]. A digital audio output [328] connects the system to digital audio devices (digital speakers, digital headphones, etc.). A battery power supply [320] powers the entire system. Depending on the communications protocol implemented (i.e. USB), the battery can be recharged through the data port interface [306].

Figure 4:
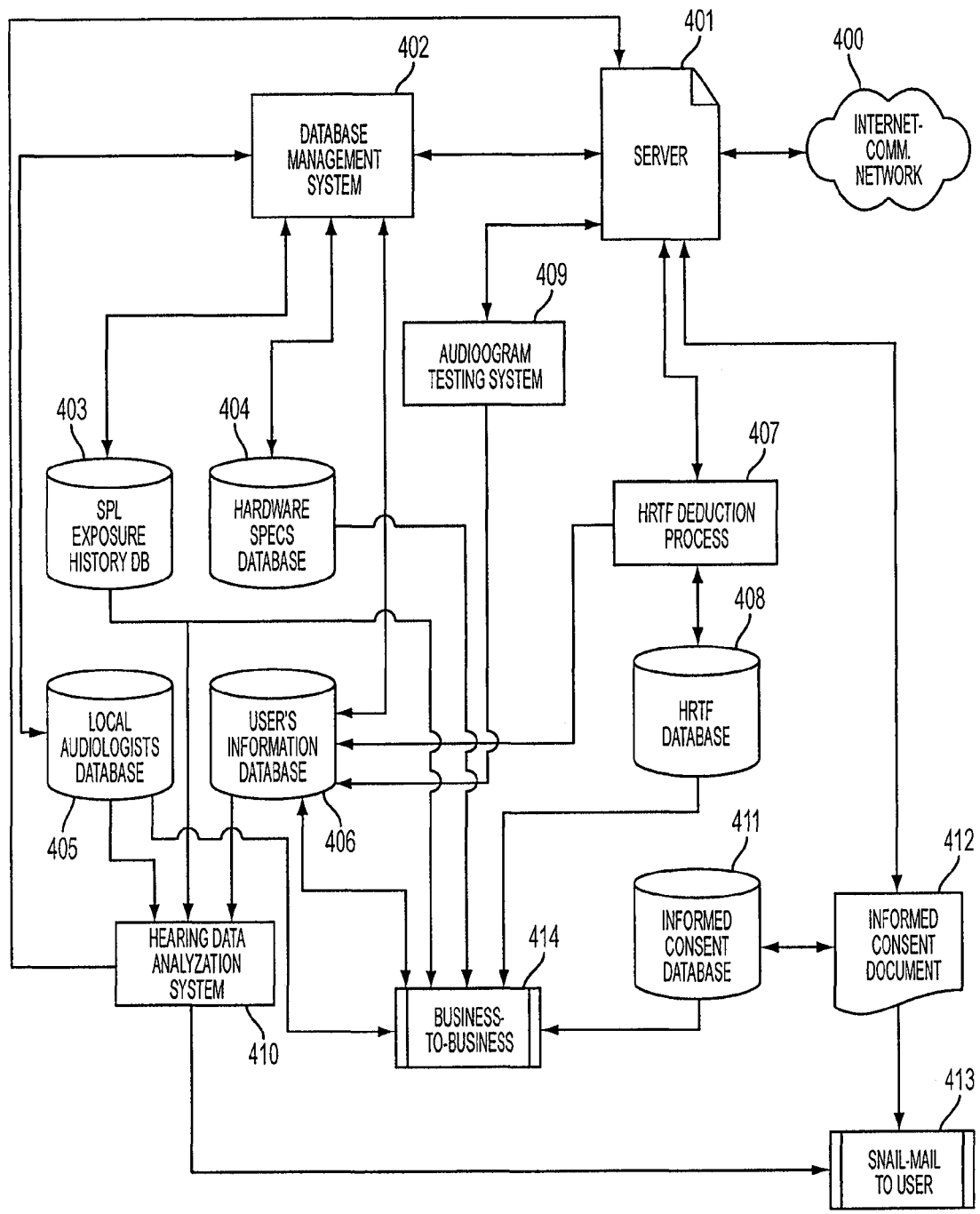
FIG. 4 illustrates in more detail the portion of the system of the present invention that operates on the server side.

A more detailed illustration of the Server system is provided in FIG. 4. A Server system [401] communicates with the data port interface of the Personal Hearing Damage Intervention system through a communications network [400] (i.e. the Internet).

The Server system [401] provides a registration interface for the user (usually in the form of a web page). During the registration process, information is solicited from the user including name, address, demographics, type of Playback Hardware, type of Headphones, and other information. This information is handled by the database management system [402] and stored in the user's information database [406].

Playback Hardware make and model information entered by a user is used to retrieve detailed characteristics from a hardware specifications database [404]. These characteristics include frequency response data, compensation filters, acoustical transducer power transfer data, the average distance from the acoustical transducer to the ear canal input, Real-Ear Level to free-field equivalent transfer functions, and other data.

As part of the registration process, an Informed Consent document [412] is presented to the user. A web-based Informed Consent document is presented to the user through the Server [401] in stages, requiring the user to agree to the terms put forth by checking a box or clicking a button. Alternatively, a hardcopy of the Informed Consent document is mailed [413] to the user. A record of users who have agreed to the Informed Consent document is stored in the informed consent database [411].

As an extension of the registration process a head-related transfer function (HRTF) deduction process is included [407]. Through this process a best-fit HRTF set is selected from a database of known HRTF sets [408]. An index to the selected HRTF set is stored in the user's information database [406].

As a further extension of the registration process a Relative Audiogram test is administered to the user with the Relative Audiogram testing system [409]. Follow-up Relative Audiogram tests are also administered through the Server using the same system. Audiogram results are stored in the user's information database [406]. More precise Audiogram data can be retrieved from audiologists (provided patient consent) through a business-to-business connection [414] and stored in the user's information database [406].

Listening Habits Histories from the data memory of the Personal Hearing Damage Intervention system are automatically uploaded to the Server anytime a connection becomes available. The database management system [402] stores Listening Habits Histories in the listening habits database [403].

Listening Habits History and Relative Audiogram(s) are analyzed using the listening history analyzation system [410] to identify potential hearing problems in users. Criteria for identifying potential hearing problems are based on audiological research and are updatable. If a potential hearing problem is identified, the user is notified electronically or by mail [413] and provided with the name, address, and phone number of a local audiologist. The audiologist information is stored in the local audiologists database [405].

Figure 5:
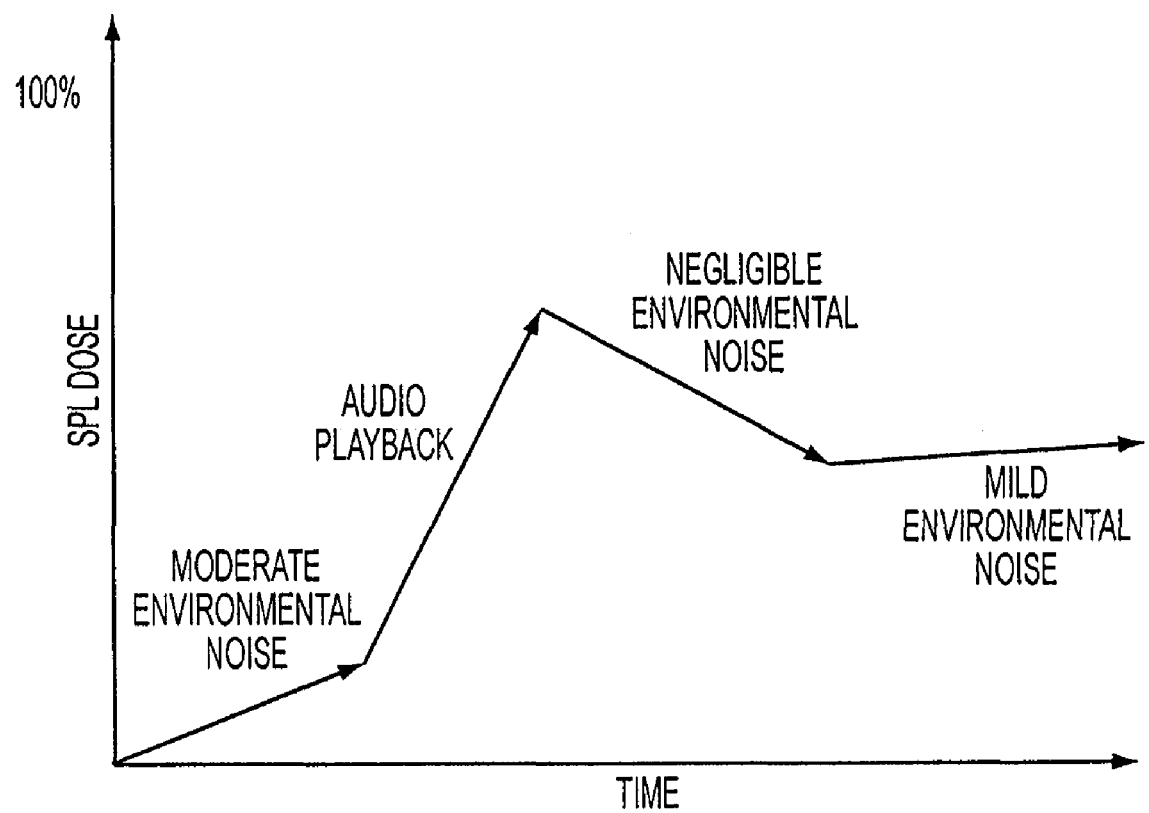
FIG. 5 illustrates an example plot of SPL Dose versus time.

Any information contained in any of the database systems can be redistributed to a third party, provided there are no privacy concerns, using a business-to-business interface [414]. An illustration of an example plot of the SPL Dose of an individual with respect to time is shown in FIG. 5. Notice how the SPL Dose will decrease when there is negligible Environmental Noise.

Further Exemplary Embodiments

At least one exemplary embodiment is directed to a Personal Hearing Damage Intervention System [104] for monitoring and reducing the potential for Hearing Damage in a user induced by both Environmental Noise and Audio Playback], the system can include any, all, or a combination of the following:

a. Analog audio inputs [303] and an analog to digital converter [301];
b. Digital audio inputs [302] using any standard or proprietary digital audio protocol (SPDIF, AES/EBU, iPod port, etc.);
c. An audio input buffer [325] and audio level monitoring system for monitoring audio signal levels and identifying audio signals that exceed some maximum "safe" threshold; Because the audio input buffer introduces a small time delay, such audio signals can be automatically Attenuated (Attenuation) before they are ever reproduced by acoustical transducers;
d. A system where a spectral analysis is preformed, allowing for several frequency bands to be monitored independently; A decision is made on the need for attenuation based on this analysis;
e. A digital timer system [314] that includes multiple timers: one activated by a minimum audio input threshold [304], and one activated by a minimum Environmental Noise threshold [312]; The timer system also tracks absolute time and date data;
f. A non-volatile updatable program memory storage system [305], containing all necessary Control Data and some default;
g. A non-volatile data memory storage system [315] for storing timer data, audio output voltage data, calculated Real-Ear Level, SPL Exposure History, and other related data;
h. A data connection system [306] for updating Control Data in the program memory (USB, BlueTooth, etc);
i. An Environmental Noise level detection system [317] (see embodiment [00164]);
j. An Environmental Noise level overload system that completely Attenuates Audio Playback and generates a warning signal (see embodiment 1) when an instantaneous Environmental Noise level threshold is exceeded;
k. A method for estimating the SPL impinging on a listener's ear generated by Audio Playback ($REL_{AP}$) based on the spectral analysis of the audio input, audio signal path levels, and a default set of acoustical transducer characteristics or, after a registration process, specific acoustical transducer characteristics (see embodiment [00170]);
l. A method for estimating the SPL impinging on a listener's ear generated by Environmental Noise ($REL_{EN}$) based on the Environmental Noise level detection system; When Audio Playback is present, the total Real-Ear Level is given by the following formula:

$$REL_{Tot} = REL_{AP} + REL_{EN}$$

Assuming the audio signal path is automatically Attenuated (Attenuation) or otherwise affected by the system, the equation becomes:

$$REL_{Tot} = REL_{AP}' + REL_{EN}$$

Assuming Acoustic Isolation Cushions are included in the system (see embodiment [00187]) or as part of a connected system (i.e. Headphones), a default set of Acoustic Isolation Cushion coefficients or specific Acoustic Isolation Cushion coefficients modify the equation further:

$$REL_{EN}' = c_{isolation} \cdot REL_{EN}$$

$$REL_{Tot} = REL_{AP}' + REL_{EN}'$$

m. A method for calculating the SPL Dose [316] for a listener from $REL_{Ear}$, timer system data, and SPL Exposure History; The exact parameters of this calculation are defined in default Control Data settings or in customized Control Data settings retrieved through a registration process (see embodiment [00158]);
n. A method for calculating a recommended maximum Safe Listening Duration [316] for a listener based on the SPL Dose calculation, $SPL_{Ear}$, and timer system data; Again, the exact parameters of this calculation are defined in default Control Data settings or in customized Control Data settings retrieved through a registration process (see embodiment [00158]);
o. A method for recording the SPL Exposure History [313] of a listener from $RE_{EN}$, $REL_{AP}$, $REL_{Tot}$, SPL Dose, and timer system data; This SPL Exposure History is stored in data memory [315]; The time-weighted average of $SPL_{EN}$ is the primary factor in the Environmental Noise Exposure History component of the SPL Exposure History; The time-weighted average of $REL_{AP}'$ is the primary factor in the Listening Habits History component of the SPL Exposure History, however spectral analysis data is also included; When accessible, metadata files describing the audio content used for Audio Playback is stored alongside the Listening Habits History component;
p. A warning signal [311] that may take the form of one or more of the following:
   i. A speech synthesis system that generates spoken messages indicating the remaining Safe Listening Duration, the amount of total listening time, the absolute time, excessive Environmental Noise, the amount of battery power remaining, or some related information;
   ii. A sample playback system that produces some prerecorded auditory alert signal or spoken message indicating the remaining Safe Listening Duration, the amount of total listening time, the absolute time, excessive Environmental Noise, the amount of battery power remaining, or some related information;
   iii. A synthesis system that produces some auditory alert signal relating to the remaining Safe Listening Duration, the amount of total listening time, the absolute time, excessive Environmental Noise, the amount of battery power remaining, or some related information;
   iv. A haptic warning system that produces some appropriate alert signal (i.e. by vibrating) relating to the Safe Listening Duration, the amount of total listening time, the absolute time, excessive Environmental Noise, the amount of battery power remaining, or some related information;
q. A display system [318] for indicating the SPL Dose and the amount of listening time left before potential Hearing Damage that may take the form of one or more of the following:
   i. A color-coded indicator patch that changes color as the user approaches 100% SPL Dose/the end of the Safe Listening Duration;
   ii. A color-coded indicator patch, an LED display, an analogue gauge, or any appropriate display that indicates the user's SPL Dose/Safe Listening Duration using as a meter, similar to a gas gauge in an automobile;
   iii. An LED display or any appropriate display that presents SPL Dose, Safe Listening Duration, remaining battery power, total listening time, absolute time, or some related information as text.

r. A digital signal processor [309] for audio signal path Attenuation, mixing audio warning signals with audio input, applying filtering to the audio signal path, and additional audio signal path processing indicated by the Control Data;

s. An optional ear canal input microphone [321] with known power transfer characteristics allowing for the direct measurement of the user's Real-Ear Level [323] to be used in the calculation of SPL Dose and Safe Listening Durations;

t. A volume control system [324] allowing the user to adjust the volume of the audio output (which also modifies the Safe Listening Duration/SPL Dose calculation);

u. A digital to analog converter [310].

At least one exemplary embodiment is directed to a Personal Hearing Damage Intervention System [104] for monitoring and reducing the potential for Hearing Damage in a user induced by both Environmental Noise and Audio Playback, the system includes a method for the user to specify the behavior of the system when their SPL Dose is exceeded. Depending on user specifications, the system behavior can include one, all, or a combination of the following:

a. Presents a series of audio warning signals [311];
b. Updates a visual display [318] with information and/or a warning message;
c. Automatically Attenuates (Attenuation) audio output using the DSP [309];
d. Stops Audio Playback entirely;
e. Generates a tactile warning (vibration, pressure, etc);
f. Generates a visual signal (e.g., flashing light); and
g. or any combination of the methods described above.

The system according to at least one further exemplary embodiment can further include one, all, or a combination of the following:

a. A modified method for calculating $REL_{Tot}$ and the SPL Dose generated by Environmental Noise without introducing any Acoustic Isolation Cushion coefficients, where:

$$REL_{Tot} = REL_{EN}$$

b. A modified method for recording SPL Exposure History where the Environmental Noise Exposure History consists of a time-weighted average of $REL_{Tot}$, timer data, and other data.

The system according to at least one further exemplary embodiment can be tailored for Headphone listening scenarios and can further include one, all, or a combination of the following:

a. A database system [404] containing information about Headphone characteristics, including the SPL output, voltage to Real-Ear Level transfer functions, the positioning of the Acoustic Transducers with respect to the listener's ear, frequency response compensation data, hardware photographs, price points, and other characteristics;

b. An interface for retrieving Headphone characteristics data from the database and inputting that data to the program memory via the data connection [400];

c. A system for retrieving Headphone characteristics data based on a unique Headphone identification number that is read when the Headphones are connected to the system;

d. The application of an appropriate Headphone frequency response compensation filter to the audio signal input using a digital signal processor [309].

At least one exemplary embodiment can be part of an earpiece or headphone system with a unique identification number. Additionally the registration system described can be part of a Personal computer system, a Personal Music Player system, a personal monitoring system, an automotive audio system, a home audio system, an avionics audio system, a personal video system, a mobile phone system, a personal digital assistant system, a standalone accessory, or an advanced eye-wear system with acoustical transducers.

Additionally separate parts of the exemplary embodiments described can be distributed among any combination of a Server system, a Personal Computer system, a Personal Music Player system, a personal monitoring system, an automotive audio system, a home audio system, an avionics audio system, a personal video system, a mobile phone system, a personal digital assistant system, a standalone accessory, or an advanced eye-wear system with acoustical transducers.

At least one exemplary embodiment can include machine learning techniques, which can be included in the SPL Dose calculation system and the SPL Exposure History system such that the Hearing Damage Intervention System is capable of learning and adapting to the listening and noise exposure patterns for a particular listener.

In at least one exemplary embodiment includes a system for the acquisition of a user's Relative Audiogram is included in the program memory [305] or data memory [315], note data can include loudness discomfort level (LDL) data.

In at least one exemplary embodiment a Relative Audiogram compensation filter is applied to audio signal path by the digital signal processor, where the system either:

a. Retrieves Relative Audiogram compensation information from a remote Server after a registration process (during transmission, the information may include HIPAA compliant encoding);

b. Or calculates a compensation filter from Relative Audiogram information obtained by the system locally.

A method for the acquisition of an individual's Relative Audiogram is described in U.S. Pat. No. 6,840,908-Edwards, U.S. Pat. No. 6,379,314-Horn, both of which are incorporated by reference in their entirety.

At least one exemplary embodiment includes Acoustic Isolation Cushions and serves as a hearing protection apparatus, informing the user of Environmental Noise exposure over time that could potentially result in Hearing Damage. An audible warning signal, some display information, a tactile warning, or some combination of the above will warn the user when the Acoustic Isolation Cushion coefficients can be insufficient for the measured Environmental Noise exposure over time (U.S. Pat. No. 6,456,199-Michael), the system further comprising:

v. A tactile sensor or user-operated switch that indicates whether or not the Headphone system is currently worn by the user;

w. A slightly modified method for monitoring and recording SPL Dose and SPL Exposure History, where:

$$REL_{EN}' = c_{isolation} \cdot REL_{EN}$$

$$REL_{Ear} = REL_{EN}'$$

In at least one exemplary embodiment the default Control Data settings correspond to a specific age range.

At least one exemplary embodiment includes a registration process, the system further comprising:

a. A system for transmitting and receiving data from the data port [306] of embodiment h, through a communications network such as the Internet [308, 400], to a Server system [401];

This system is most commonly a software application running on a Client Personal Computer connected to the Internet; Mobile phone networks, or other communication systems could also be used;

b. A registration interface querying the user to collect registration information including demographic information, age, gender, Playback Hardware information, Headphone information, occupational information, home and work locations, and other information;

c. A Server system [401] for storing, retrieving, and disseminating Control Data updates, registration information, and any other relevant information.

In at least one exemplary embodiment an Informed Consent form [412] is included as part of the registration process, the system further comprising:

x. An interface system for presenting the facts and implications associated with the use of the present invention in one or more stages, requiring the user to somehow indicate they agree with the conditions (usually by checking a box or clicking a button on a web interface);

y. A hardcopy letter [413] presenting the facts and implications associated with the use of the present invention;

z. A database system [411] containing information about Informed Consent agreements available through a web interface.

In at least one exemplary embodiment the Control Data is transmitted from the Server system to the system based on the registration information provided by the user. Updates to the Control Data may include modification of minimum input threshold parameters, acoustical transducer characteristics, the dB V to dB SPL transfer function, SPL Dose calculation parameters, SPL Exposure History parameters, the time-weighted average noise exposure calculation parameters, the function relating time-weighted average noise exposure to Safe Listening Durations and SPL Dose, ear recovery function parameters, Generic, Personalized, or Semi-Personalized HRTF data, and any filtering parameters that relate to Audiogram compensation, inverse Headphone response, personal preferences, audiological recommendations or other data.

In at least one exemplary embodiment a Relative Audiogram acquisition process is included as part of the registration process, and a Relative Audiogram compensation filter is included as part of the Control Data updates. Audiogram data can be encoded and decoded for transmission using a HIPAA compliant encoding system.

In at least one exemplary embodiment a fast HRTF deduction process is included as part of the registration process, and Semi-Personalized HRTF data is included as part of the Control Data updates.

In at least one exemplary embodiment a Personalized HRTF data is measured and used instead of Semi-Personalized HRTF data, by any method familiar to those skilled in the art.

A least one exemplary embodiment includes a system for the detection of Environmental Noise levels (for example U.S. Pat. No. 6,456,199-Michael), the system comprising:

aa. An input Acoustic Transducer or input Acoustic Transducers;

bb. Any system for monitoring audio signal levels, familiar to those skilled in the art;

cc. A method for compensating for the Acoustic Isolation Cushion characteristics of a given Headphone system;

dd. Always on behavior, allowing for the constant measurement of Environmental Noise;

ee. Data outputs connecting to the digital signal processor [309], the SPL Dose/Safe Listening Duration calculation [316], and the SPL Exposure History system for recording Environmental Noise Exposure Histories.

In at least one exemplary embodiment the system includes some active noise cancellation system familiar to those skilled in the art (e.g., U.S. Pat. No. 6,925,620-Elzing a, U.S. Pat. No. 6,912,286-Daly).

In at least one exemplary embodiment the input acoustical transducers are connected to the audio signal path at the DSP through the Environmental Noise detection system, allowing the user to audition Environmental Audio (i.e. speech, music), mitigating the need for the user to remove the associated Headphone apparatus to audition to Environmental Audio, and can further include one, all, or a combination of the following:

I. A stereo pair of input Acoustical Transducers [327] placed close to the user's ear canal input (as described by the Ear Mould Styles), preserving spatialization cues and achieving or approximating binaural recording conditions to create an Environmental Audio input signal;

II. A spatial audio system [329] for supplementing the spatial cues captured by the stereo pair of input Acoustical Transducers to provide improved spatial perception of Environmental Audio using any combination of the following methods:
   a. The application of Generic, Semi-Personalized, or Personalized HRTF data to the environmental audio input signal;
   b. The application of binaural enhancement algorithms, familiar to those skilled in the art, to the environmental audio input signals;
   c. The application of a pinna simulation algorithm to the environmental audio input signal;
   d. A synthetic pinna apparatus placed just before the stereo input acoustical transducers;

III. A method for compensating for the non-linear frequency response characteristics of the Acoustical Isolation Cushions of a given Headphone system by applying corresponding inverse filters to the Environmental Audio input signal at the DSP; With this method, the system acts as a linear-frequency-response hearing protection apparatus;

IV. A system for first Attenuating Audio Playback and then mixing the environmental audio input signals, at a louder volume, with the audio signal path using the DSP, where the system is activated by any combination of the following methods:
   e. A manual switch to activate/deactivate the system;
   f. A speech detection apparatus, included as part of the Environmental Noise level detection system, to activate the system when speech is detected as the principal component of the Environmental Audio input;

V. A system for noise cancellation that can be customized through the registration process (see embodiment [00160]) to better meet the user's specific needs (i.e. occupation-related noise cancellation); A typical application would be a special set of noise cancellation parameters tuned to the drilling equipment used by a dentist.

At least one exemplary embodiment includes a database system [404] containing information about Headphone characteristics, including SPL output, input voltage to Real-Ear Level transfer functions, the positioning of the Acoustic Transducers with respect to the listener's ear, frequency response compensation data, hardware photographs, price points, and other characteristics.

In at least one exemplary embodiment the database also contains information about a broader range of Playback Hardware including personal music players, loudspeakers, amplifiers, for example current and past models with hardware and acoustic characteristics.

At least one exemplary embodiment can include a software system [307] for interfacing with various other systems in exemplary embodiments, the software system can include one, all, or a combination of the following:
- ff. An interface allowing the user to specify the type of Playback Hardware he/she intends to use;
- gg. A method for retrieving relevant Playback Hardware characteristics from a database over a communications network [308];
- hh. A system for automatically retrieving Control Data updates from a Server [401] over a communications network [308, 400];
- ii. A communications system [306] for exchanging relevant Control Data with the program memory of another element or system.

At least one exemplary embodiment can include a method for estimating the Real-Ear Level generated by Audio Playback based on audio output levels and default or specific acoustical transducer characteristics, the system can include one, all, or a combination of the following:
- jj. A default output voltage to Real-Ear Level transfer function, corresponding to some generic acoustical transducer characteristics;
- kk. A method for retrieving relevant Playback Hardware characteristics, such as acoustical transducer output specifications and the position of the acoustical transducers with respect to the listener's ear, from a database;
- ll. A method for estimating the distance from the listener's ears to the acoustical transducers from information in a database;
- mm. A customized output voltage to Real-Ear Level transfer function, corresponding to some specific acoustical transducer characteristics.

At least one exemplary embodiment can include a method for the fast acquisition of Semi-Personalized HRTF data via a deduction process [407], the method can include one, all, or a combination of the following:
- I. A database system [408] containing indexed, clustered HRTF data sets;
- II. An auditory test signal with distinctive spatial characteristics, where two or more distinct sound source locations exist;
- III. A system for the application of potential HRTF matches to the auditory test signal;
- IV. A feedback system, allowing the user to select the best listening experience from a number of candidate listening experiences, based on the spatial quality perceived in the HRTF-processed auditory test signal.

In at least one exemplary embodiment the data connection system [306] makes use of some wireless communications protocol (e.g., 802.11, BlueTooth, etc.) to transmit and receive digital audio data for playback, and can include one, all, or a combination of the following:
- I. An audio codec to encode and decode digital audio transmissions;
- II. A wireless communications system (802.11, BlueTooth, etc.) for transmitting and receiving data (digital audio transmissions, Control Data, SPL Exposure History, etc.);
- III. A method for pairing two or more SPL monitoring systems through a wireless communications protocol to provide a secure exchange of data.

In at least one exemplary embodiment the system enables listeners to share digital audio transmissions, and can include one, all, or a combination of the following:
- nn. A method for scanning for available digital audio transmissions within range;
- oo. A method for employing the system as a relay-rebroadcasting digital audio transmissions to increase wireless range.

In at least one exemplary embodiment multiple systems are capable of sharing the contents of their program and data memory, allowing for the tracking of Listening Habits Histories across multiple devices.

At least one exemplary embodiment can be applied to a scenario where users might require information dissemination and/or hearing protection. Examples of application scenarios include hearing protection and communication in the industrial workplace, unobtrusive communication on a television or video production set, and hearing protection and monitoring for performing musicians.

At least one exemplary embodiment includes an automatic language translation system [330] for converting speech signals in the Environmental Audio input signals to speech signals of another language delivered to the user through the audio signal path, and can include one, all, or a combination of the following:
- pp. A speech recognition system familiar to those skilled in the art;
- qq. A language translation system familiar to those skilled in the art;
- rr. A speech synthesis engine for synthesizing translated speech, familiar to those skilled in the art.

At least one exemplary embodiment includes a function for tracking SPL

Exposure Histories across multiple Headphone systems, making use of unique Headphone identification numbers.

At least one exemplary embodiment includes a system for automatically collecting, storing, and redistributing SPL Exposure Histories, and can include one, all, or a combination of the following:
- i. An SPL monitoring and adjustment system, which stores SPL Exposure History in the data memory and transmits SPL Exposure History data through the data port [306] over a communications network [308] to a Server [401];
- ii. A Server system [401] for receiving and collecting SPL Exposure Histories from a SPL monitoring and adjustment system;
- iii. An SPL monitoring and adjustment system that sends SPL Exposure Histories to a Server any time the data port is connected to a communications network capable of connecting with the Server;
- iv. A database system [403] for storing SPL Exposure History alongside any information collected during the registration process.

At least one exemplary embodiment includes a combination of the SPL Exposure History data collected by the system and user work/home location information included in the registration data allows for the approximate measurement of noise pollution in these locations.

At least one exemplary embodiment can include a reporting system [410] that analyzes statistical trends in SPL Exposure Histories, Relative Audiograms, and registration information across many users and many demographics, and provides information to a given user relating their personal SPL Exposure History, Relative Audiogram results, professional referral, and registration information to statistical trends.

At least one exemplary embodiment includes a system [410] that automatically sends a notification to a registered user indicating when the said user should re-take an Relative Audiogram test, the system can include one, all, or a combination of the following:

ss. An electronic notification in the form of an email, text message, or other digital transmission sent to the user;
 tt. A hardcopy notification mailed to the user;
 uu. A method for the acquisition of a user's Relative Audiogram over a communications network;
 vv. Some incentive for the user to take an Relative Audiogram test;
 ww. A professional referral system, encouraging users to take more comprehensive full Audiogram tests through a local audiologist;
 xx. A scheduling system for using the information contained in a database system to determine when a particular user should retake a Relative Audiogram test.

At least one exemplary embodiment can include a system for updating default Control Data and user-specific Control Data based on new research, or new audiological, medical, governmental, or other standards relating to Hearing Damage, exposure to noise over time, or exposure to music over time.

At least one exemplary embodiment can include a method for automatically notifying users about potential hearing problems and directing the user to a local audiologist, the system can include one, all, or a combination of the following:

i. A Relative Audiogram acquisition process as part of a user registration process that encourages periodic re-testing;
 ii. A system [410] for comparing Relative Audiogram results to previous Relative Audiogram results, as well as to baseline Audiogram data, to identify potential hearing problems;
 iii. A database system [405] containing information about licensed audiologists in different areas;
 iv. An electronic notification in the form of an email, text message, or other digital transmission sent to the user; and
 v. A hardcopy notification mailed to the user.

At least one exemplary embodiment can include a method for retrieving relevant data from an audiologist regarding a specific user's hearing given the user's consent.

At least one exemplary embodiment can include a system for redistributing the contents or statistical analysis of any of the database systems described in the above embodiments through some business-to-business conduit [414] to interested parties, the system can include one, all, or a combination of the following:

yy. An interface allowing interested parties to query all of the database systems and retrieve information provided appropriate compensation; This interface system can take the form of a web page;
 zz. A system for restricting access to sensitive personal information or information of a medical nature.

In at least one exemplary embodiment signal processing techniques are used to reduce the potential for Hearing Damage for a given audio signal without significantly altering how the audio signal is perceived by the listener, the system can include one, all, or a combination of the following:

aaa. A total harmonic distortion measurement system operating on the DSP;
 bbb. A transient acoustical power reduction system operating on the DSP;
 ccc. A listening duration-dependent filtering system operating on the DSP;
 ddd. A loudness compression system based upon personal Loudness Discomfort Level (LDL) data operating of the DSP.

In at least one exemplary embodiment the end user is able to select an Acoustical Isolation Cushion attachment that best fits the anthropometrics of the said user's ear, the system can include one, all, or a combination of the following:

I. Several Acoustic Isolation Cushion attachments, designed for different ear shapes and sizes, which provide improved isolation from ambient noise; alternatively, referral to obtain custom molded acoustic isolation cushions via earmold impressions and a designated earmold manufacturing laboratory;
 II. An Environmental Noise detection system, that compensates for the type of Acoustic Isolation Cushion attachment the end user selects; and
 III. A body-conducted noise detection system, the output of which can be used to compensate for the occlusion effect, in which an increase in low frequency energy is observed the ear canal, a source of user complaints when an occluding hearing instrument is placed in the ear (e.g., such as a CIC hearing aid).

In at least one exemplary embodiment the audio content can be retrieved from a communications network through the data port and stored in the program memory [305] or data memory [315] for later playback.

At least one exemplary embodiment can include a digital timer system which acts as a clock, informing the user of the current time through the display system, a synthesized speech signal, or a combination of both, the system can include one, all, or a combination of the following:

eee. A system for synchronizing the digital timer system [314] to a Server using the data port [306] and some communications network [308]; and
 fff. An interface allowing the user to query the system for the current time.

At least one exemplary embodiment can include a microphone for the capture of a user's speech or other auditory stimuli, allowing the system to be applied to any communications scenario (i.e. as a mobile phone accessory). The microphone input can be recorded and saved in data memory.

In at least one exemplary embodiment the microphone input can be stored in data memory for later retrieval, facilitating the use of at least one device as a personal audio recorder. For example a user can activate the device (e.g., snapping of fingers, voice command, touch) to record a particular amount of time (e.g. 30 seconds), which can be replayed and/or stored. For example a device in accordance with at least one exemplary embodiment can comprise:

a.) A system that can record audio segments from a microphone input to be written from an audio input buffer [325] into the program memory or data memory for later playback;
 b.) A system where audio segments can be recorded using the microphone input to be "time-stamped" according to the digital timer system [314] when the related audio data is written from the audio input buffer [325] into the program memory [305] or data memory [315] for later playback;
 c.) A system that lets a user select recorded audio segments for playback based upon index information provided by a digital timer system [314];
 d.) An interface allowing the user to transfer recorded audio segments to a Server [401] using the data port [306] and some communications network [308]; and
 e.) An interface letting a user to begin to store audio data held in audio input buffer [325] beginning with audio data sampled several seconds earlier than the time at which the user triggers the buffered recording feature (ear sticky).

Figure 6A:
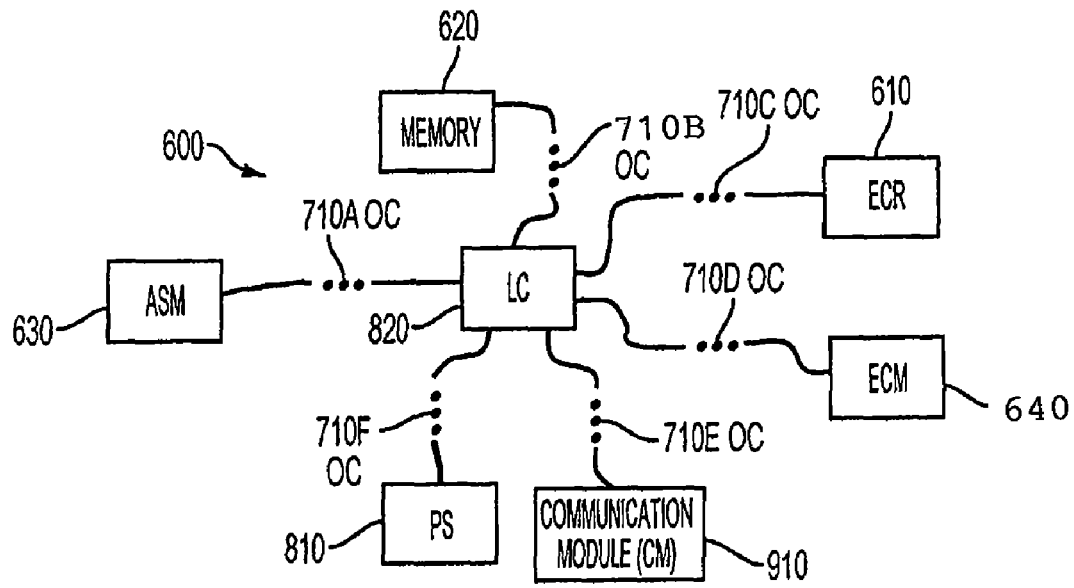
FIGS. 6A and 6B illustrate examples of at least one exemplary embodiment of a device that can be attached to an audio device (e.g., Ipod™, BlackBerry™ smartphone, cell phone, headphone, earpiece, and other devices that can emit an audio signal either directly (e.g., via a transducer), or direct a drive signal that can be converted into an audio signal).
Figure 6B:
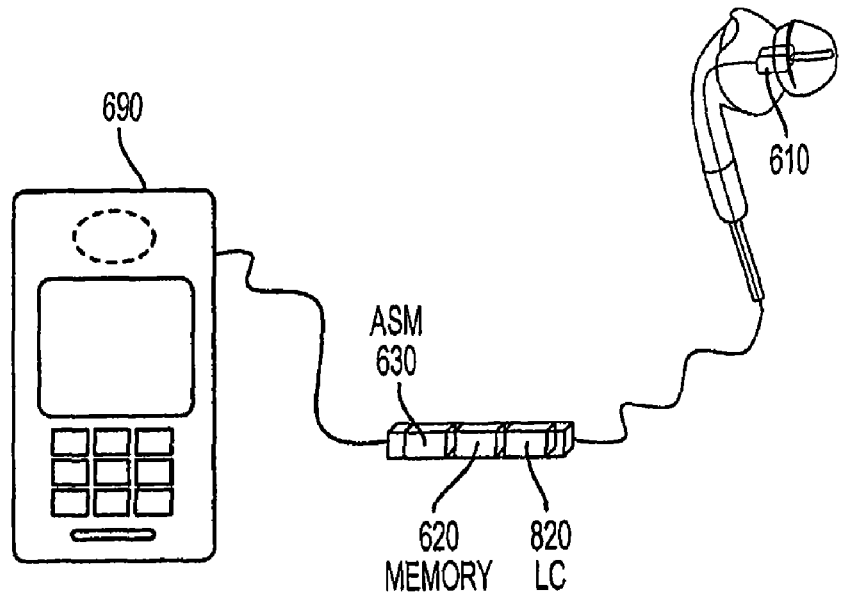

At least one exemplary embodiment is illustrated in FIGS. 6A and 6B. For example FIG. 6A illustrates a self-contained version of an earpiece 600 according to at least one exemplary embodiment, including a power source (PS) 810 (e.g., zinc-air battery (ZeniPower A675P), Li-ion battery), and a logic circuit 820 (LC, e.g., Gennum Chip GA3280) in addition to ear canal receiver (ECR) 610, ear canal microphone (ECM) 640, memory 620 and ambient sound microphone (ASM) 630. Earpiece 600 can also include a wireless module 910 for wireless communications or can be wired. Earpiece 600 can also connect remotely to various parts (e.g., via a wired or wireless connection). For example FIG. 6B illustrates an earpiece that is connected to a separate device that inputs a drive signal from an audio device 690, optionally measures the ambient sound pressure level (SPL) by an ambient sound microphone (ASM) 630, and optionally includes a logic circuit 820 to measure sound pressure level dose. For example the earpiece can be an earbud that includes ECR 610 (FIG. 6B), whose signals travel back and forth via a wire that is operatively connected (OC) 710C to LC 820, which in turn can be operatively connected 710F to PS 810 (e.g., which can be in an audio device 690). ASM 630 can be operatively connected 710A to LC 820, memory 620 can be operatively connected 710B to LC 820, ECM 640 can be operatively connected 710D to LC 820 and communication module (CM) 910 can be operatively connected 710E to LC 820. Note that ECR 610 can also be a dual purpose ECR/ECM, where when the receiver function (ECR mode) is not used the microphone function (ECM mode) can be used. For example U.S. Pat. No. 3,987,245 discusses a dual-purpose transducer that can be used as a microphone and/or a receiver.

In at least one further exemplary embodiment a recording feature can be activated where the ASM records the ambient environment (e.g., a person talking, a sound, other recordable audio sounds) and can download the recorded content as a way file or some other recordable format, and can be replayed.

At least one exemplary embodiment is directed to a method of monitoring sound pressure level comprising: measuring a first sound pressure level in the ear canal; measuring a second sound pressure level out of the ear canal; calculating a first sound pressure level dose using the first sound pressure level; and calculating a second sound pressure level dose using the second sound pressure level.

The method can further compare at least one of the first sound pressure level dose and the second sound pressure level dose with a threshold sound pressure level dose.

At least one further exemplary embodiment includes sending a notification signal to a user when the threshold sound pressure level dose is exceeded by at least one of the first sound pressure level dose or the second sound pressure level dose. For example if an ASM is used to calculate approximately what an ear without an earpiece experiences as a SPL Dose and the ECM measures what is experienced by the ear with an earpiece, when either SPL Dose (i.e., using the ASM or the ECM measured values) exceeds a threshold value, the user can receive an auditory notification to cover the unprotected ear or to stop playing audio content in the ear with the earpiece. Thus in at least one exemplary embodiment a first sound pressure dose is indicative of the sound pressure level dose of a first ear and a second sound pressure dose is indicative of the sound pressure level dose of a second ear.

At least one further exemplary embodiment is directed to a device, which can be in an earpiece, in an audio player, attached to a headphone (e.g., earbuds) or otherwise attached to input a drive signal that can be used to generate audio signals, that calculates the SPL equivalent of the drive signal, can calculate an equivalent SPL Dose, and modify the drive signal to decrease its contribution to the SPL Dose. The device can be separately attached to a headphone and data can be stored and retrieved later, or downloaded via the headphone wires. The device can also include a microphone which can measure whatever environment the device is in and approximate an environmental SPL Dose experienced by a user, which when added to the SPL Dose equivalent of the drive signal provides a total SPL Dose.

The device can further query any attached device (e.g., an audio device such as a headphone) to obtain identification (e.g., make and model), which can be used to query a stored table to retrieve noise attenuation data for the attached device (e.g., NRR of 25 dB for a headphone). The device can further use the noise attenuation data to improve any SPL Dose calculation. For example if the SPL Dose is calculated by using only the signal measured by an ASM, then the SPL measured can be reduced by the noise attenuation value (e.g., 25 dB noise reduction rating (NRR), Note this can be frequency dependent). Additionally if the location of the ASM is known relative to a person's ear, a transform function can relate measurements from the ASM to equivalent values in the ear canal, and these values can be used to calculate SPL Dose, along with the noise attenuation data.

At least one exemplary embodiment is directed to a method of sound pressure level measurement comprising: calculating a sound pressure level equivalent for a drive signal; calculating a sound pressure level for a measured signal; calculating a total sound pressure level dose from a total sound pressure level, where if the total sound pressure level is less than a permissible sound level then a recovery function is used in calculation of the total sound pressure level dose; comparing the total sound pressure level dose to a threshold value; and modifying the drive signal if the total sound pressure level dose exceeds the threshold value, where if a new total sound pressure level dose is calculated using the modified drive signal the new total sound pressure level dose is less than the threshold value.

At least one exemplary embodiment includes a device that can be part of an earpiece or attached to other devices (e.g., Ipod™) where a user can activate a record mode, where audio signals picked up by at least one microphone in the device can be recorded for a selected or designed period of time (e.g., seconds, minutes, hours). Recording can be locally on the device (e.g., RAM) or downloaded and stored remotely (e.g., on a computer hard drive)

Recording can be initiated by a user by various means, for example a distinctive sound trigger (e.g., snapping fingers), pushing a button. The stored audio content can be replayed via the same user interface (e.g. snapping fingers, touching a button etc.) or by other methods (e.g., mouse click on a GUI).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A method of monitoring a sound pressure level comprising:
measuring a first sound pressure level in an ear canal;
measuring a second sound pressure level external to the ear canal;
calculating a first sound pressure level dose using the first sound pressure level when the first sound pressure level is greater than a permissible sound level, where the first sound pressure level dose increases above the permissible sound level and decreases below the permissible sound level;

calculating the first sound pressure level dose using a recovery function to model the decrease of the first sound pressure level dose when the first sound pressure level is below the permissible sound level; and calculating a second sound pressure level dose using the second sound pressure level.

2. The method according to claim 1, further comprising:
comparing at least one of the first sound pressure level dose and the second sound pressure level dose with a threshold sound pressure level dose.

3. The method according to claim 2, further comprising:
sending a notification signal to a user when the threshold sound pressure level dose is exceeded by at least one of the first sound pressure level dose or the second sound pressure level dose.

4. The method according to claim 3, where the first sound pressure level dose is indicative of a sound pressure level dose of a first ear.

5. The method according to claim 4, where the second sound pressure dose is indicative of a sound pressure level dose of a second ear.

6. The method according to claim 5, where the notification signal is an auditory signal sent to the user to switch an earpiece from the first ear to the second ear.

7. The method according to claim 1, where the first sound pressure level is generated by at least one of an ambient environment, an ear receiver, and a user's voice.

8. A sound pressure level monitoring device comprising:
a first input port for receiving a first input signal; and
a logic circuit, where the logic circuit calculates a sound pressure level equivalent of the first input signal, calculates a sound pressure level dose using the sound pressure level equivalent when the sound pressure level equivalent is greater than a permissible sound level, and calculates the sound pressure level dose using a recovery function to model a decrease of the sound pressure level dose when the sound pressure level equivalent is below the permissible sound level, where the sound pressure level dose increases above the permissible sound level and decreases below the permissible sound level.

9. The device according to claim 8, where the first input signal is sent by the logic circuit as a first output, signal.

10. The device according to claim 9, where the logic circuit identifies a receiver that receives the first output signal.

11. The device according to claim 10, where the logic circuit identifies the receiver by the logic circuit sending a query signal and the logic circuit receiving a return signal, where the return signal is used to identify the receiver.

12. The device according to claim 11, where the logic circuit queries a look-up table using the identity of the receiver to obtain a noise reduction rating.

13. The device according to claim 12, where the logic circuit uses the noise reduction rating along with the first input signal to calculate the sound pressure level equivalent.

14. The device according to claim 13, further comprising:
a microphone.

15. The device according to claim 14, where a second input signal is obtained by the microphone.

16. The device according to claim 15, where the logic circuit uses the noise reduction rating along with the first input signal and the second input signal to calculate the sound pressure level equivalent.

17. The device according to claim 13, where the device is attached to an audio device.

18. The device according to claim 16, where the device is attached to an audio device.

19. The device according to claim 18, where the audio device is a headphone.

20. The device according to claim 18, where the audio device is a communication device.

21. The device according to claim 18, where the audio device is an audio playing device.

22. A method of sound pressure level measurement comprising:
calculating a sound pressure level equivalent for a drive signal;
calculating a sound pressure level for a measured signal;
calculating a total sound pressure level dose from a total sound pressure level using the sound pressure level equivalent and the sound pressure level when the total sound pressure level is greater than a permissible sound level, the total sound pressure level dose increasing above the permissible sound level and decreasing below the permissible sound level;
calculating the total sound pressure level dose using a recovery function to model the decrease of the total sound pressure level dose when the total sound pressure level is less than the permissible sound level;
comparing the total sound pressure level dose to a threshold value; and
modifying the drive signal if the total sound pressure level dose exceeds the threshold value, where if a new total sound pressure level dose is calculated using the modified drive signal the new total sound pressure level dose is less than the threshold value.

23. The method according to claim 22, where the measured signal is from a microphone.

* * * * *